United States Patent [19]
Tanimura et al.

[11] Patent Number: 5,665,338
[45] Date of Patent: Sep. 9, 1997

US005665338A

[54] HAIR TREATMENT COMPOSITION

[75] Inventors: Tadashi Tanimura, Sakura; Yoshiko Tabata, Tokyo, both of Japan

[73] Assignee: Kao Corporation, Tokyo, Japan

[21] Appl. No.: 550,517

[22] Filed: Oct. 30, 1995

Related U.S. Application Data

[63] Continuation of Ser. No. 151,844, Nov. 15, 1993, abandoned.

[30] Foreign Application Priority Data

Nov. 30, 1992 [JP] Japan ................................. 4-320348

[51] Int. Cl.$^6$ ....................................................... A61K 7/09
[52] U.S. Cl. ............................................ 424/70.51; 424/70.5
[58] Field of Search ................................... 424/70.51, 70.5

[56] References Cited

U.S. PATENT DOCUMENTS

| | | | |
|---|---|---|---|
| 5,041,283 | 8/1991 | Kita et al. | 424/64 |
| 5,200,175 | 4/1993 | Tabata et al. | 424/70 |

*Primary Examiner*—Jyothsan Venkat
*Attorney, Agent, or Firm*—Oblon, Spivak, McClelland, Maier & Neustadt, P.C.

[57] ABSTRACT

A hair treatment composition comprising (A) a keratin-reducing substance; and (B) a nonionic amphiphatic compound which contains at least one long-chain branched alkyl or alkenyl group per molecule, and which has an HLB of 2–12, the compound itself or a mixture of the compound and water maintaining a liquid crystal structure at a temperature ranging from 0°–50° C. The composition possesses excellent moisturizability, smoothness and softness, exhibits a remarkably high conditioning effect which is sustainable, and exhibits the effects of reducing damage to the hair and preventing the occurrence of split hairs, and imparting gloss to the hair.

11 Claims, No Drawings

HAIR TREATMENT COMPOSITION

This application is a Continuation of application Ser. No. 08/151,844, filed on Nov. 15, 1993, now abandoned.

BACKGROUND OF THE INVENTION

1. Field of the Invention

The present invention relates to hair treatment compositions, and more specifically to hair treatment compositions which possess excellent moisturizability, smoothness and softness, which exhibit a very high conditioning effect, which can be sustained, and which reduces damage to the hair, prevents the occurrence of split hairs, and imparts gloss to the hair, all of which can be sustained.

2. Description of the Background

The use of a keratin-reducing substance to reduce the hair has been proposed, thereby sustainably setting the hair or causing a specific substance to penetrate into or adhere to the hair in order to change the properties of the hair. The reduction of the hair with the keratin-reducing substance makes it possible to maintain the effects of these treatments, but raises the problem that the hair may suffer irreversible damage, thereby impairing the strength, appearance and feel of the air.

Therefore, conditioning components and/or moisterizers have been added to the conventional hair treatments which contain a keratin-reducing substance. However, the effects of these additives are temporary and are not sustainable.

For example, an approach which is known is to incorporate a cationic polymer in a first-package permanent wave formulation and an anionic surfactant in a second-package permanent wave formulation (Japanese Patent Application Laid-Open No. 100710/1981). In another method an anionic surfactant or amphoteric surfactant is placed in a first-package permanent wave formulation and a cationic cellulose derivative is incorporated in a second-package permanent wave formulation (Japanese Patent Publication No. 24322/1992). Japanese Patent Application Laid-Open No. 110611/1989 discloses a formulation of Amodimethicone and a cationic surfactant in a first-package permanent wave formulation and a carboxylic acid type anionic surfactant in a second-package permanent wave formulation. However, these permanent wave compositions are not entirely satisfactory since they exhibit poor sustainability, though they are recognized to have the effects of reducing damage to the hair and of improving the feel of the hair to the touch to some extent. In addition, the use of Amodimethicone in a permanent hair-waving system is accompanied by the problem that it has the adverse effect of not imparting sufficient control to the hair. A need therefore continues to exist for the development of a hair treatment formulation which exhibits an excellent conditioning effect which can be sustained.

SUMMARY OF THE INVENTION

Accordingly, one object of the invention is to provide a hair treatment composition which exhibits excellent moisturizability, smoothness and softness, which exhibits a remarkably high conditioning effect which can be sustained, and which exhibits the effects of reducing damage to the hair and preventing the occurrence of split hairs, and imparting gloss to the hair, all of which can be sustained.

Briefly, this object and other objects of the invention as hereinafter will become more readily apparent can be attained by a hair treatment composition comprising (A) a keratin-reducing substance, and (B) a nonionic amphiphatic compound which contains at least one long-chain branched alkyl or alkenyl group per molecule, and has an HLB of 2–12, the compound itself or a mixture of said compound and water maintaining a liquid crystal structure at any temperature of 0°–50° C.

DETAILED DESCRIPTION OF THE PREFERRED EMBODIMENTS

The keratin-reducing substance (component (A)) is a substance which has a reducing ability against keratin which is a structural protein for the hair. No particular limitation is imposed on such keratin-reducing substances so long as they are generally used in hair treatments. Examples thereof include thioglycolic acid, derivatives thereof and salts thereof; cysteine, derivatives thereof and salts thereof; thiolactic acid and salts thereof; sulfurous acid and salts thereof; bisulfites; thioglyceryl alkyl ethers, derivatives thereof and salts thereof; and mercaptoalkyl-amides, derivatives thereof and salts thereof. Derivatives of thioglycolic acid include glyceryl monothioglycolate and the like. Preferred examples of the salts of thioglyclic acid and derivatives thereof include the ammonium salts, primary amine salts such as the monoethanolamine salts, secondary amine salts such as the diethanolamine salts, tertiary amine salts such as the triethanolamine salts, alkali metal salts such as the sodium and potassium salts, and alkaline earth metal salts such as the calcium salts. The derivatives of cysteine include N-acyl-L-cysteines, wherein the number of carbon atoms of the acyl group ranges from 2–18, preferably 2–12, and the like. Preferred examples of salts of cysteine and derivatives thereof include the hydrochlorides. Preferred examples of the thiolactates include the ammonium salt, monoethanolamine salt, triethanolamine salt, and alkali metal salts such as the sodium and potassium salts. Preferred examples of the sulfites include the ammonium salt, and alkali metal salts such as the sodium and potassium salts. Preferred examples of the bisulfites include the ammonium salt, and alkali metal salts such as the sodium and potassium salts. Suitable derivatives of the thioglyceryl alkyl ethers include ethoxyhydroxypropanethiol, ethoxyethoxyhydroxypropanethiol, isopropoxyethoxyhydroxypropanethiol and the like. Suitable derivatives of the mercaptoalkylamides include mercaptoethylpropanamide, mercaptoethylglyconamide and the like.

Of these, thioglycolic acid and salts thereof, cysteine and salts thereof, cysteine derivatives such as the N-acyl-L-cysteines, sulfurous acid and the salts thereof, and the bisulfites are particularly preferred.

In the present invention, these keratin-reducing substances (component (A)) may be used either singly or in any combination thereof. In general, the proportion of component (A) used may preferably be within a range of 0.1–20.0 wt. % (hereinafter indicated simply as "%") based on the whole hair treatment composition, although the proportion varies according to the kind of the reducing substance and the pH of the composition.

The nonionic amphiphatic compound (component (B)) of the present invention is required to contain at least one long-chain branched alkyl or alkenyl group per molecule, and have an HLB of 2–12. The compound itself or its mixture with water is also required to keep a liquid crystal structure at any temperature in the range of 0°–50° C. It is hence not preferable to use any nonionic amphiphatic compound having an HLB value outside the above range. An HLB range of 3–10 is particularly preferred.

Incidentally, the term "HLB" is an index which indicates hydrophilic-lipophilic balance. In the present invention, HLB values are obtained by calculation in accordance with the following equation by Oda, Teramura et al.

$$HLB = \frac{\Sigma \text{ inorganic value}}{\Sigma \text{ organic value}} \times 10$$

The temperature range over which the liquid crystal structure of the nonionic amphipatic compound is kept intact is from 0° to 50° C., preferably from 5° to 40° C., more preferably from 5° to 35° C. In the present invention, the liquid crystal structure may be either a lamellar liquid crystal structure or an inverse middle liquid crystal structure according to the kind of nonionic amphipatic compound used. Confirmation of the lamellar liquid crystal structure can be achieved by means of X-ray diffraction and differential scanning calorimetry (DSC) in accordance with, for example, the methods described in The Journal of Cell Biology, 12, 207–209, and "Hyomen", 11(10), 579–590.

Examples of the nonionic amphipatic compounds which form a lamellar liquid crystal structure include the following compounds (B-1) through (B-4):

(B-1):

Glycerylated polyols represented by the following formula (1):

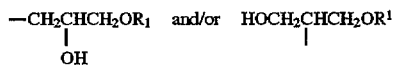  (1)

wherein G is the residue of hydroxyl groups which have been eliminated from a polyol selected from the group consisting of pentaerythritol, sorbitol, maltitol, glucose, and fructose, A denotes a group

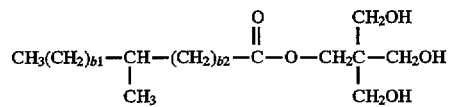

in which $R^1$ is a branched alkyl or alkenyl group having 10–36 carbon atoms, and a stands for a number of 1 or greater, but not exceeding the total number of the hydroxyl groups in the polyol;

(B-2):

Methyl-branched fatty acid esters represented by the following formula (2):

$$CH_3(CH_2)_{b1}-\underset{CH_3}{\underset{|}{CH}}-(CH_2)_{b2}-\overset{O}{\underset{}{\overset{\|}{C}}}-O-CH_2\underset{CH_2OH}{\underset{|}{C}}-CH_2OH \quad (2)$$

wherein $b_1$ and $b_2$ stand individually for 0 or an integer from 1 to 33, and the sum of $b_1$ and $b_2$ is 6–33;

(B-3):

Branched fatty acid glyceroglicolipids represented by the following formula (3):

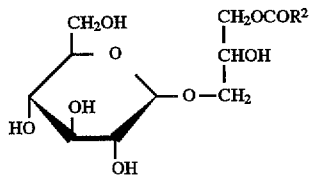  (3)

wherein $R^2$ is

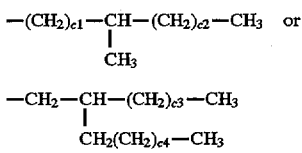

in which $c_1$ and $c_2$ stand individually for zero or an integer of 1 to 33, the sum of $c_1$ and $c_2$ is 6–33, $c_3$ and $c_4$ stand individually for zero or an integer of 1 to 31, and the sum of $c_3$ and $c_4$ is 4–31; and (B-4):

Alkyl trismethylols represented by the following formula (4) or alkyl trismethylolamides represented by the following formula (5):

$$R^3-C(CH_2OH)_3 \quad (4)$$

$$R^3-CONHC(CH_2OH)_3 \quad (5)$$

wherein $R^3$ means a linear or branched alkyl group having 6–22 carbon atoms.

In the glycerylated polyols (B-1), the alkylglycosides expressed by G in formula (1) include methylglycoside, ethylglycoside, propylglycoside, octylglycoside, methylmaltoside, ethylmaltoside and the like. $R^1$ may preferably be a branched alkyl group having 16–36 carbon atoms, particularly 18–24 carbon atoms. Such a branched alkyl group $R^1$ may preferably be a group represented by the following formula (6) or (7):

  (6)

  (7)

in which $c_1$ and $c_2$ have the same meaning as defined above. Suitable examples of these branched alkyl groups include methylpentadecyl, methylhexadecyl, methylheptadecyl (isostearyl), methyloctadecyl, methylbehenyl, ethylhexadecyl, ethyloctadecyl, ethylbehenyl, butyldodecyl, butylhexadecyl, butyloctadecyl, hexyldecyl, heptylundecyl, octyldodecyl, decyldodecyl, decyltetradecyl, dodecylhexadecyl and tetradecyloctadecyl groups, and the like. a in the formula (1) is preferably 1 or 2.

The glycerylated polyol (1) is prepared, for example, by reacting a polyol and its corresponding branched alkyl glycidyl ether (8) in the presence of a basic catalyst in accordance with the following reaction formula:

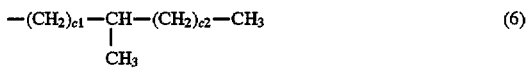  (1)

(8)

wherein $R^1$ has the same meaning as defined above.

The molar ratio of the polyol to the branched alkyl glycidyl ether (8) in this reaction may be suitably selected according to the etherification degree of the intended glycerylated polyol. For example, in order that an intended glycerylated polyol having 1 mol of the glycidyl ether added thereto may be provided in a high content, in general, it is only necessary to use the polyol in excess at a ratio of 1.2:1.0 to 10.0:1.0. Taking the amount of the 1-mol adduct formed and recovery of the polyol into consideration, it is preferable to use the polyol in a ratio of 1.5:1.0 to 5.0:1.0. Besides, in order that the glycerylated polyol having 2 mols of glycidyl ether added thereto may be provided in a high content, in general, it is only necessary to use the branched alkyl glycidyl ether in excess at a ratio of 0.3:1.0 to 1.1:1.0. Taking the amount of the 2-mol adduct formed into consideration, the ether is preferably used in a ratio of 0.4:1.0 to 0.8:1.0.

Although the reaction may be generally conducted without using any solvent, it is preferable to use an organic solvent for the purpose of facilitating the mixing of the polyol with the branched alkyl glycidyl ether. Examples of such an organic solvent include dimethyl sulfoxide, dimethylacetamide, dimethylformamide and N-methylpyrrolidone. Preferably, the solvent is used in an amount 0.1 to 10.0 times the polyol.

As a catalyst, any acid or basic catalyst generally employed as a catalyst for the reaction of an epoxy group be used. However, the use of an acid catalyst is not preferred, because acid catalysts can catalyze the decomposition of the glycerylated polyol at ether linkages and by dehydration of hydroxyl groups as side reactions. It is hence preferable to use a basic catalyst. The type of basic catalyst employed is not limited. From the viewpoint of reactivity and economy, however, sodium hydroxide, potassium hydroxide, sodium methylate, sodium ethylate, sodium hydride and the like are desirable. These basic catalysts may preferably be used in a range of 0.01–20.0%, particularly 0.1–10.0% based on the polyol.

The reaction is conducted at 50°–200° C., preferably 80°–150° C. If the reaction temperature is less than 50° C., the reaction rate becomes slow. If the reaction temperature exceeds 200° C., a colored product is formed. It is hence not preferable to conduct the reaction at any temperature outside the above range.

Incidentally, in this reaction, the epoxy group in the branched alkyl glycidyl ether reacts with water to form a glyceryl ether as a by-product, if water is present in the reaction system. Therefore, the branched alkyl glycidyl ether is preferably added to the polyol for reaction after water is removed from the polyol by dissolving or dispersing the polyol in an organic solvent and blowing dry nitrogen gas into the solution or dispersion under heat, or heating the polyol under reduced pressure to dehydrate it.

After completion of the reaction, for example, an organic acid such as acetic acid or citric acid, or an inorganic acid such as sulfuric acid, hydrochloric acid or phosphoric acid is added to the reaction mixture to neutralize the catalyst, and the organic solvent used in the reaction is then removed. The organic solvent may preferably be removed generally at a temperature of 120° C. or lower under reduced pressure in order to avoid the thermal decomposition of the reaction product. The glycerylated polyol (1) useful in the practice of this invention is generally provided as a mixture containing, in addition to a 1-mol adduct in which a molecule of the branched alkyl glycidyl ether (8) is added to a molecule of the polyol and a 2-mol adduct in which 2 molecules of the branched alkyl glycidyl ether (8) are added to a molecule of the polyol, multi-mol adducts in which 3 or more molecules of the branched alkyl glycidyl ether (8) are added to a molecule of the polyol. The glycerylated polyol (1) is generally used in the form of a mixture of the 1-mol, 2-mol and multi-mol adducts thus obtained. If a problem occurs for reasons of performance and its incorporation into a product composition, these adducts may be separately purified by means of a known purification method such as column chromatography on silica gel or solvent extraction. The glycerylated polyol (1) may contain an unreacted glycoside in addition to the intended 1-mol, 2-mol and multi-mol adducts in some cases. The glycerylated polyol (1) may be used in the presence of unreacted glycoside unless it causes problems in practical use. If the unreacted glycoside however causes problems, it can be removed by a known purification method such as, for example, a two-phase extraction solvent system with an organic solvent such as ethyl acetate, methyl ethyl ketone, methyl isobutyl ketone or chloroform, or a thin film distillation.

In formula (2) representing the methyl-branched fatty acid ester (B-2), the sum of $b_1$ and $b_2$ is 6–33. However, the sum preferably is 10–16, most preferably 14 from the viewpoint of performance as a cosmetic material. It is particularly preferred that the branched methyl group be located near the center of the alkyl main chain.

The methyl-branched fatty acid ester (2) is prepared by the following reaction:

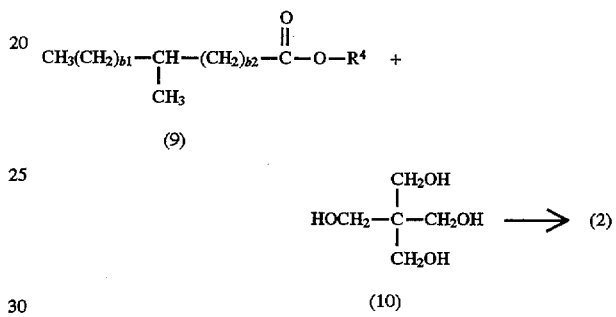

wherein $b_1$ and $b_2$ have the same meanings as defined above, and $R^4$ denotes an alkyl group having 1–18 carbon atoms, preferably an alkyl group having 1–3 carbon atoms.

More specifically, pentaerythritol (10) is reacted with a lower alkyl ester (9) of a methyl-branched fatty acid, thereby preparing the intended compound (2).

The lower alkyl ester (9) of the methyl-branched fatty acid used in this reaction is obtained by esterifying the methyl branched carboxylic acid by a method known per se in the art. Suitable carboxylic acid reactants in particular are industrial products prepared as a mixture of acids in a certain distribution in the total number of carbon atoms in the hydrocarbon portion of the molecules and the position of the branched methyl group. For example, isostearic acid obtained as a by-product upon preparation of an oleic acid dimer is a mixture containing about 75% or more of acids having 18 carbon atoms in total (the sum of $b_1$ and $b_2$:14), the remainder being those respectively having 14, 16 and 20 carbon atoms in total. Their branched methyl groups are located substantially in the center of the hydrocarbon main chain [J. Amer. Oil Chem. Soc., Vol. 51, 522 (1974)].

In this reaction, the molar ratio of the lower alkyl ester (9) of the methyl-branched fatty acid to be used to pentaerythritol (10) is preferably 1:1 to 10:1.

No particular limitation is imposed on solvents which are employed in the reaction. However, solvents dissolving both lower alkyl ester (9) of the methyl-branched fatty acid and pentaerythritol (10) therein are preferred. For example, dimethylformamide may preferably be used.

As the catalyst for the reaction, an alkali catalyst is generally used. Sodium methylate or the like is preferred. No particular limitation is imposed on the amount of the catalyst. It is however preferable to use the catalyst in a range of 0.1–20 mol% based on the lower alkyl ester (9) of the methyl-branched fatty acid. The reaction temperature in this reaction is selected within the range of 60–150° C.

The isolation of the compound (2) may be conducted by a method known per se in the art, for example, by distillative removal of solvent by recrystallization or chromatography, or a combination thereof.

In the formula (3), which represents the branched fatty acid glyceroglycolipid (B-3), the sum of $c_1$ and $c_2$ in $R^2$ may preferably be 10–16, particularly 14 from the viewpoint of performance as a cosmetic material, as with $b_1$ and $b_2$ described above. On the other hand, the sum of $c_3$ and $c_4$ may preferably be 6–14, particularly 8–12 from the same viewpoint described above.

The branched fatty acid glyceroglycolipid (3) is prepared, for example, by following reaction formula:

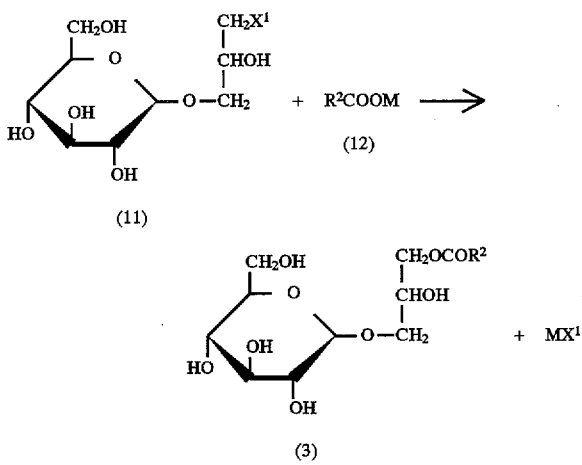

wherein $X^1$ is halogen, M is hydrogen or a cationic group, and $R^2$ has the same meaning as defined above.

More specifically, a fatty acid (12) is reacted with compound (11), thereby preparing compound (3).

The compound (11) used in this reaction can be easily prepared by a known method, for example, by reaction of a monosaccharide or oligosaccharide with a glycerol monohalohydrin, glycerol dihalohydrin or epihalohydrin.

The compound (12) can be prepared, for example, by reacting a fatty acid and an alkali metal hydroxide such as sodium hydroxide, or an amine in the presence of a suitable solvent. Incidentally, examples of the cationic group designated by M in compound (12) include alkali metal atoms, ammonium ion, alkylammonium ions and trialkanolamine radicals.

In the practice of this process, it is only necessary, for example, to react compound (11) and compound (12) at a temperature of 0°–150° C., preferably 30°–120° C. The amount of compound (12) used in this reaction is generally 0.3–3.0 mols, most preferably 1.0–2.0 mols per mol of the compound (11). If M in the compound (12) is a hydrogen atom, the reaction is conducted in the presence of an alkaline substance. Examples of alkaline substances include alkali metal hydroxides such as sodium hydroxide and potassium hydroxide, alkali metal alcoholates, and alkylamine hydroxides.

In the practice of this reaction, a polar solvent may be used for the purpose of facilitating the nixing of compound (11) and compound (12) and allowing the reaction to proceed smoothly. Suitable polar solvents useful in this reaction include at least one compound selected from the group of dimethylformamide, dimethylacetamide, dimethyl sulfoxide, N-methylpyrrolidone, pyridine, water and the like. The amount of the polar solvent to be used may be suitably chosen. In the practice of this reaction, if necessary, it is possible to use a phase-transfer catalyst for the purpose of allowing the reaction to proceed smoothly. The amount of the phase transfer catalyst used in this reaction may be suitably chosen. However, the amount is generally 0.1–10 mol % based on compound (12). Examples of the phase-transfer catalyst used herein include tetraalkylammonium chlorides such as tetraethylammonium bromide, tetrapropylammonium bromide, tetrabutylammonium bromide, tetraheptylammonium bromide, tetrahexylammonium bromide, N,N,N-trimethyl-N-octylammonium chloride, N,N,N-trimethyl-N-decylammonium chloride, N,N,N-trimethyl-N-dodecylammonium chloride, N,N,N-trimethyl-N-hexadecylammonium chloride, N,N,N-trimethyl-N-octadecylammonium chloride, N,N-dimethyl-N,N-hexyldecyl-ammonium chloride and N,N-dimethyl-N,N-dioctadecylammonium chloride.

The reaction mixture in the above reaction generally contains, in addition to the intended glyceroglycolipid (3) inorganic salts as by-products, unreacted compound (11) and/or compound (12), and the like. Therefore, although the reaction mixture may be used as is according to the intended application of the resulting composition, the glyceroglycolipid may be purified for use by a known method such as, for example, partition chromatography, adsorption chromatography, solvent fractionation, recrystallization or the like, if it must be provided as a highly purified product.

The compounds (B-1) through (B-4) thus obtained are thermotropic liquid crystals whose lamellar liquid crystal structure is kept at a temperature ranging from 0°–50° C., and have good properties such that when they are mixed with water, they are almost evenly dispersed as lamellar liquid crystals in water. In order to form such a liquid crystal structure, it is only necessary to control the proportion of water to such a compound within the range of from $^{99}/_1$ to $^1/_{99}$ by weight.

On the other hand, examples of the nonionic amphipatic compounds forming an inverse middle liquid crystal structure include α-mono(methyl-branched alkyl) glyceryl ethers represented by the following formula (13):

$$R^5—OCH_2CH(OH)CH_2OH \qquad (13)$$

wherein $R^5$ is a methyl-branched saturated hydrocarbon group having 9–36 carbon atoms, and may preferably be a group represented by the following formula:

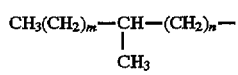

in which m and n are each individually a value ranging from 0–33, and the sum of m and n is 6–33.

The α-mono(methyl-branched alkyl) glyceryl ether (13) can be prepared by, for example, the method described in Japanese Patent Publication No. 26997/1986 or 1368/1987. The nonionic amphiphatic compound (13) forms an even inverse middle liquid crystal structure at any temperature ranging from 0°–50° C. when mixed with water. In order to form such a liquid crystal structure, it is only necessary to control the proportion of water to such a compound within a range of from $^{99}/_1$ to $^1/_{99}$ by weight.

These nonionic amphipatic compounds (B) may be used either singly or in any combination thereof, and may preferably be incorporated in a hair treatment composition in an amount of 0.05–10%, particularly 0.1–10%, based on the whole composition. Any amounts less than 0.05% result in a composition which fails to exhibit sufficient effects. On the other hand, any amounts exceeding 10.0% result in a hair treatment composition having a sticky feel to the touch. It is hence not preferable to use compound (B) in any amount outside the above range.

Additives, which are used routinely in hair cosmetic compositions, for example, various surfactants, oily substances, moisturizers, hair protecting agents, feel improvers, coloring matter, perfume bases, thickeners, solubilizing agents, ultraviolet absorbents, antiphlogistics and hair-growing ingredients, may be incorporated in the hair treatment compositions of the invention within limits which do not impede the effects of the present hair treatment composition.

The pH of the hair treatment composition of the present invention is preferably within the range of 3.0–9.5, preferably 4.0–9.0. Any pH value less than 3.0 or higher than 9.5 is not preferred because the skin and hair may possibly be damaged.

The hair treatment composition of the present invention can be formulated as a permanent wave composition, straight permanent wave composition, sustainable hair-setting composition, sustainable hair-curing composition, curled hair-straightening composition or the like in accordance with methods known per se in the art. It may also be formulated as an intermediate treatment composition and after treatment composition.

In the present invention, although both keratin-reducing substance (A) and nonionic amphiphatic compound (B) may be mixed with each other in the same formulation, these ingredients may be incorporated in different formulations to successively treat the hair. For example, they may be formulated as follows:

First-package formulation (containing A and B)/second-package formulation;

First-package formulation (containing A)/second-package formulation (containing B);

First-package formulation (containing A)/intermediate treatment formulation (containing B)/second-package formulation; and First-package formulation (containing A)/second-package formulation/after treatment formulation (containing B).

In the case of a two-pack curing composition, the ingredients may be incorporated in a shampoo/rinse system.

Having generally described this invention, a further understanding can be obtained by reference to certain specific examples which are provided herein for purposes of illustration only and are not intended to be limiting unless otherwise specified.

SYNTHETIC EXAMPLE 1

A 500-ml flask is charged with 82 g of pentaerythritol, 200 g of dimethyl sulfoxide and 1 g of sodium hydroxide. The contents are heated to 105° C. to form a solution. Dry nitrogen gas is blown into the flask to distill off about 20 g of water and dimethyl sulfoxide, thereby removing water from the reaction system. After 39 g of isostearyl glycidyl ether are added dropwise to the residual reaction mixture over 1 hour, the contents are reacted at 105° C. for 4 hours with stirring.

After completion of the reaction, 1.5 g of acetic acid are added to the reaction mixture to neutralize the catalyst, and dimethyl sulfoxide is completely removed at 80° C. under reduced pressure. To the residue is added 99% ethanol and unreacted pentaerythritol is removed by filtration. After ethanol is distilled from the resulting filtrate under reduced pressure, 500 ml of water and 500 ml of ethyl acetate are added to the residue for extraction with ethyl acetate. The solvent is distilled from the resultant ethyl acetate-soluble fraction to yield 63 g of a crude pale yellow adduct of pentaerythritol with isostearyl glycidyl ether.

The crude product is subjected to separation and purification by column chromatography on silica gel making use of a 2:1 mixed elution solvent of acetone and hexane, thereby eluting the intended adduct of pentaerythritol with 1 mol of isostearyl glycidyl ether. The eluate fractions are collected to remove the solvent by distillation, thereby yielding 16 g (yield: 30%) of the intended adduct of pentaerythritol with 1 mol of isostearyl glycidyl ether.

Hydroxyl value: 482 (calculated value: 486).

NMR (CDCL$_3$): δ (ppm) 3.95(1H, m, —OCH$_2$—C HOH—CH$_2$O—), 3.67(6H, s, —C(CHOH)$_3$), 3.46(8H, m, —OCH$_2$—), 1.30–1.59(29H, b, —CH$_2$—, —CH—), 0.88 (6H, m, —CH$_3$).

IR (liquid film) cm$^{-1}$: $v_{O-H}$ (—OH) 3200–3400 $v_{O-H}$ (stretching) (—CH—, —CH$_2$—, —CH$_3$) 2850, 2920 $v_{O-H}$ (deformation) (—CH—, —CH$_2$—, —CH$_3$) 1375, 1460 $v_{O-H}$ (—C—O—) 1110, 1035, 1010.

SYNTHETIC EXAMPLE 2

A reaction is conducted in the same manner as described in Synthetic Example 1 to prepare 63 g of a crude adduct of pentaerythritol with isostearyl glycidyl ether.

The crude product is subjected to gel permeation chromatography. As a result, it is confirmed that the crude product is a mixture of a pentaerythritol monoether having 1 mol of isostearyl glycidyl ether added thereto, a pentaerythritol diether having 2 mols of isostearyl glycidyl ether added thereto, a pentaerythritol triether having 3 mols of isostearyl glycidyl ether added thereto and a pentaerythritol tetraether having 4 mols of isostearyl glycidyl ether added thereto. The compositional proportions of the monoether, diether, triether and tetraether were found to be 77%, 19%, 3% and 1%, respectively, from the ratio of their peak areas.

Hydroxyl value: 438.

IR (liquid film) cm$^{-1}$: $v_{O-H}$ (—OH) 3200–3400 $v_{O-H}$ (stretching) (—CH—, —CH$_2$—, —CH$_3$) 2850, 2920 $v_{O-H}$ (deformation) (—CH—, —CH$_2$—, —CH$_3$) 1375, 1460 $v_{C-O}$(—C—O—) 1110, 1035, 1010.

EXAMPLE 1

Permanent wave compositions of the corresponding formulations shown in Tables 1 through 7 were prepared by a method known per se in the art to conduct organoleptic evaluation right after treating the hair with the compositions and after shampooing the treated hair 10 times. The results are shown in Table 8.

(Evaluation method)

Tresses of 15 g in weight were subjected to permanent waving by the conventional method by each of ten hairdressers. Immediately after the permanent waving and after shampooing the treated tresses 10 times with a plain shampoo, each permanent wave composition was evaluated with respect to ease of combing in a wet state, and softness, smoothness, gloss and moisturizability in a dry state. Moreover, the surface appearance of the hair and the shape of waves are ranked as A=excellent, B=good, C=slightly poor, or D=poor. The ranking is in terms of average values.

TABLE 1

| Ingredient % | Invention Product 1 | 2 | 3 |
|---|---|---|---|
| First Package: | | | |
| Ammonium thioglycolate solution (containing 50% of thioglycolic acid) | 14 | — | 1.8 |
| N-Acetyl-L-cysteine | — | 10 | — |
| L-Cysteine | — | — | 6 |
| Ethoxyhydroxypropanethiol | — | — | — |
| Sodium sulfite | — | — | — |
| Polyoxyethylene (10) lauryl ether sodium phosphate | — | — | — |
| Lauryldimethylaminoacetic acid betaine | — | — | — |
| Amodimethicone | — | — | — |
| Stearyltrimethylammonium chloride | — | — | — |
| Sodium N-lauroyl-N-methyl-β-alanine | — | — | — |
| Adduct of pentaerythritol with 1 mol of isostearyl glycidyl ether (Synthetic Example 1) | 3 | 3 | 3 |
| Monoethanolamine | ←Proper Amount→ | | |
| Purified water | ←Balance→ | | |
| Total | 100 | 100 | 100 |
| Ph | 9 | 9 | 9 |
| Second-package: | | | |
| Sodium bromate | 8 | 8 | 8 |
| Cationic cellulose derivative | — | — | — |
| Amodimethicone | — | — | — |
| Stearyltrimethylammonium chloride | — | — | — |
| Sodium N-lauroyl-N-methyl β-alanine | — | — | — |
| Adduct of pentaerythritol with 1 mol of isostearyl glycidyl ether (Synthetic Example 1) | 3 | 3 | 3 |
| Sodium hydroxide (48%) | 1 | 1 | 1 |
| Citric acid | ←Proper Amount→ | | |
| Purified water | ←Balance→ | | |
| Total | 100 | 100 | 100 |
| pH | 7 | 7 | 7 |

TABLE 2

| Ingredient % | Invention Product 4 | 5 | 6 |
|---|---|---|---|
| First Package: | | | |
| Ammonium thioglycolate solution (containing 50% of thioglycolic acid) | — | — | 14 |
| N-Acetyl-L-cysteine | — | — | — |
| L-Cysteine | — | — | — |
| Ethoxyhydroxypropanethiol | 14 | — | — |
| Sodium sulfite | — | 4 | — |
| Polyoxyethylene (10) lauryl ether sodium phosphate | — | — | — |
| Lauryldimethylaminoacetic acid betaine | — | — | — |
| Amodimethicone | — | — | — |
| Stearyltrimethylammonium chloride | — | — | — |
| Sodium N-lauroyl-N-methyl-β-alanine | — | — | — |
| α-Monoisostearyl glyceryl ether | 3 | 3 | — |
| Monoethanolamine | ←Proper Amount→ | | |
| Purified water | ←Balance→ | | |
| Total | 100 | 100 | 100 |
| pH | 9 | 9 | 9 |
| Second-package: | | | |
| Sodium bromate | 8 | 8 | 8 |
| Cationic cellulose derivative | — | — | — |
| Amodimethicone | — | — | — |
| Stearyltrimethylammonium chloride | — | — | — |
| Sodium N-lauroyl-N-methyl β-alanine | — | — | — |
| α-Monoisostearyl glyceryl ether | 3 | 3 | — |
| Sodium hydroxide (48%) | 1 | 1 | 1 |
| Citric acid | ←Proper Amount→ | | |
| Purified water | ←Balance→ | | |
| Total | 100 | 100 | 100 |
| pH | 7 | 7 | 7 |

TABLE 3

| Ingredient % | Invention Product 7 | 8 | 9 |
|---|---|---|---|
| First Package: | | | |
| Ammonium thioglycolate solution (containing 50% of thioglycolic acid) | — | 1.8 | — |
| N-Acetyl-L-cysteine | 10 | — | — |
| L-Cysteine | — | 6 | — |
| Ethoxyhydroxypropanethiol | — | — | 14 |
| Sodium sulfite | — | — | — |
| Polyoxyethylene (10) lauryl ether sodium phosphate | — | — | — |
| Lauryldimethylaminoacetic acid betaine | — | — | — |
| Amodimethicone | — | — | — |
| Stearyltrimethylammonium chloride | — | — | — |
| Sodium N-lauroyl-N-methyl-β-alanine | — | — | — |
| Adduct of pentaerythritol with oleyl glycidyl ether | 3 | 3 | 3 |
| Monoethanolamine | ←Proper Amount→ | | |
| Purified water | ←Balance→ | | |
| Total | 100 | 100 | 100 |
| pH | 9 | 9 | 9 |
| Second-package: | | | |
| Sodium bromate | 8 | 8 | 8 |
| Cationic cellulose derivative | — | — | — |
| Amodimethicone | — | — | — |
| Stearyltrimethylammonium chloride | — | — | — |
| Sodium N-lauroyl-N-methyl β-alanine | — | — | — |
| Adduct of pentaerythritol with oleyl glycidyl ether | — | — | — |
| Sodium hydroxide (48%) | 1 | 1 | 1 |
| Citric acid | ←Proper Amount→ | | |
| Purified water | ←Balance→ | | |
| Total | 100 | 100 | 100 |
| pH | 7 | 7 | 7 |

TABLE 4

| Ingredient % | Invention Product 10 | 11 | 12 |
|---|---|---|---|
| First Package: | | | |
| Ammonium thioglycolate solution (containing 50% of thioglycolic acid) | — | 14 | — |
| N-Acetyl-L-cysteine | — | — | 10 |
| L-Cysteine | — | — | — |
| Ethoxyhydroxypropanethiol | — | — | — |
| Sodium sulfite | 4 | — | — |
| Polyoxyethylene (10) lauryl ether sodium phosphate | — | — | — |
| Lauryldimethylaminoacetic acid betaine | — | — | — |
| Amodimethicone | — | — | — |
| Stearyltrimethylammonium chloride | — | — | — |

TABLE 4-continued

|  | Invention Product | | |
|---|---|---|---|
| Ingredient % | 10 | 11 | 12 |
| Sodium N-lauroyl-N-methyl-β-alanine | — | — | — |
| Adduct of pentaerythritol with pentadecyl glycidyl ether | 3 | — | — |
| Monoethanolamine | ←Proper Amount→ | | |
| Purified water | ←Balance→ | | |
| Total | 100 | 100 | 100 |
| pH | 9 | 9 | 9 |
| Second-package: | | | |
| Sodium bromate | 8 | 8 | 8 |
| Cationic cellulose derivative | — | — | — |
| Amodimethicone | — | — | — |
| Stearyltrimethylammonium chloride | — | — | — |
| Sodium N-laurayl-N-methyl β-alanine | — | — | — |
| Adduct of pentaerythritol with pentadecyl glycidyl ether | — | 3 | 3 |
| Sodium hydroxide (48%) | 1 | 1 | 1 |
| Citric acid | ←Proper Amount→ | | |
| Purified water | ←Balance→ | | |
| Total | 100 | 100 | 100 |
| pH | 7 | 7 | 7 |

TABLE 5

|  | Invention Product | | |
|---|---|---|---|
| Ingredient % | 13 | 14 | 15 |
| First Package: | | | |
| Ammonium thioglycolate solution (containing 50% of thioglycolic acid) | 1.8 | — | — |
| N-Acetyl-L-cysteine | — | — | — |
| L-Cysteine | 6 | — | — |
| Ethoxyhydroxypropanethiol | — | 14 | — |
| Sodium sulfite | — | — | 4 |
| Polyoxyethylene (10) lauryl ether sodium phosphate | — | — | — |
| Lauryldimethylaminoacetic acid betaine | — | — | — |
| Amodimethicone | — | — | — |
| Stearyltrimethylammonium chloride | — | — | — |
| Sodium N-lauroyl-N-methyl-β-alanine | — | — | — |
| Adduct of pentaerythritol with isostearyl glycidyl ether (Synthetic Example 2) | — | — | — |
| Monoethanolamine | ←Proper Amount→ | | |
| Purified water | ←Balance→ | | |
| Total | 100 | 100 | 100 |
| pH | 9 | 9 | 9 |
| Second-package: | | | |
| Sodium bromate | 8 | 8 | 8 |
| Cationic cellulose derivative | — | — | — |
| Amodimethicone | — | — | — |
| Stearyltrimethylammonium chloride | — | — | — |
| Sodium N-lauroyl-N-methyl β-alanine | — | — | — |
| Adduct of pentaerythritol with isostearyl glycidyl ether (Synthetic Example 2) | 3 | 3 | 3 |
| Sodium hydroxide (48%) | 1 | 1 | 1 |
| Citric acid | ←Proper Amount→ | | |
| Purified water | ←Balance→ | | |
| Total | 100 | 100 | 100 |
| pH | 7 | 7 | 7 |

TABLE 6

|  | Invention Product | | |
|---|---|---|---|
| Ingredient % | 1 | 2 | 3 |
| First Package: | | | |
| Ammonium thioglycolate solution (containing 50% of thioglycolic acid) | 14 | 14 | — |
| N-Acetyl-L-cysteine | — | — | 10 |
| L-Cysteine | — | — | — |
| Ethoxyhydroxypropanethiol | — | — | — |
| Sodium sulfite | — | — | — |
| Polyoxyethylene (10) lauryl ether sodium phosphate | 5 | — | — |
| Lauryldimethylaminoacetic acid betaine | 5 | — | — |
| Amodimethicone | — | 2 | — |
| Stearyltrimethylammonium chloride | — | 0.1 | — |
| Sodium N-lauroyl-N-methyl-β-alanine | — | 0.15 | — |
| Adduct of pentaerythritol with isostearyl glycidyl ether (Synthetic Example 2) | — | — | — |
| Monoethanolamine | ←Proper Amount→ | | |
| Purified water | ←Balance→ | | |
| Total | 100 | 100 | 100 |
| pH | 9 | 9 | 9 |
| Second-package: | | | |
| Sodium bromate | 8 | 8 | 8 |
| Cationic cellulose derivative | 2 | — | — |
| Amodimethicone | — | 2 | — |
| Stearyltrimethylammonium chloride | — | 0.1 | — |
| Sodium N-lauroyl-N-methyl β-alanine | — | 0.15 | — |
| Adduct of pentaerythritol with isostearyl glycidyl ether (Synthetic Example 2) | — | — | — |
| Sodium hydroxide (48%) | 1 | 1 | 1 |
| Citric acid | ←Proper Amount→ | | |
| Purified water | ←Balance→ | | |
| Total | 100 | 100 | 100 |
| pH | 7 | 7 | 7 |

TABLE 7

| Ingredient % | Comparative Product 4 |
|---|---|
| First Package: | |
| Ammonium thioglycolate solution (containing 50% of thioglycolic acid) | 1.8 |
| N-Acetyl-L-cysteine | — |
| L-Cysteine | 6 |
| Ethoxyhydroxypropanethiol | — |
| Sodium sulfite | — |
| Polyoxyethylene (10) lauryl ether sodium phosphate | — |
| Lauryldimethylaminoacetic acid betaine | — |
| Amodimethicone | — |
| Stearyltrimethylammonium chloride | — |
| Sodium N-lauroyl-N-methyl-β-alanine | — |
| Adduct of pentaerythritol with isostearyl glycidyl ether (Synthetic Example 2) | — |
| Monoethanolamine | ←Proper Amount→ |
| Purified water | ←Balance→ |
| Total | 100 |
| pH | 9 |
| Second-package: | |
| Sodium bromate | 8 |
| Cationic cellulose derivative | — |
| Amodimethicone | — |
| Stearyltrimethylammonium chloride | — |
| Sodium N-lauroyl-N-methyl β-alanine | — |
| Adduct of pentaerythritol with isostearyl glycidyl ether (Synthetic Example 2) | — |

TABLE 7-continued

| Ingredient % | Comparative Product 4 |
|---|---|
| Sodium hydroxide (48%) | 1 |
| Citric acid | ←Proper Amount→ |
| Purified water | ←Balance→ |
| Total | 100 |
| pH | 7 |

TABLE 8

|  | Invention Product | | | | | | | | | | | | | | | Comparative Product | | | |
|---|---|---|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 | 1 | 2 | 3 | 4 |
| Organoleptic evaluation right after treatment | | | | | | | | | | | | | | | | | | | |
| Ease of combing in wet state | A | A | A | A | A | A | A | A | A | A | A | A | A | A | A | B | B | D | D |
| Softness in dry state | A | A | A | A | A | A | A | A | A | A | A | A | A | A | A | B | B | D | D |
| Smoothness in dry state | A | A | A | A | A | A | A | A | A | A | A | A | A | A | A | B | B | D | D |
| Gloss in dry state | A | A | A | A | A | A | A | A | A | A | A | A | A | A | A | B | B | D | D |
| Moisturizability in dry state | A | A | A | A | A | A | A | A | A | A | A | A | A | A | A | B | B | D | D |
| Surface appearance of the hair | A | A | A | A | A | A | A | A | A | A | A | A | A | A | A | B | B | D | D |
| Shape of waves | A | A | A | A | B | A | A | A | A | B | A | A | A | A | B | A | B | A | A |
| Organoleptic evaluation after shampooing 10 times | | | | | | | | | | | | | | | | | | | |
| Ease of combing in wet state | B | B | B | B | B | B | B | B | B | B | B | B | B | B | B | C | C | D | D |
| Softness in dry state | B | B | B | B | B | B | B | B | B | B | B | B | B | B | B | C | C | D | D |
| Smoothness in dry state | B | B | B | B | B | B | B | B | B | B | B | B | B | B | B | C | C | D | D |
| Gloss in dry state | B | B | B | B | B | B | B | B | B | B | B | B | B | B | B | C | C | D | D |
| Moisturizability in dry state | B | B | B | B | B | B | B | B | B | B | B | B | B | B | B | C | C | D | D |
| Surface appearance of the hair | B | B | B | B | B | B | B | B | B | B | B | B | B | B | B | C | C | D | D |
| Shape of waves | B | B | B | B | B | B | B | B | B | B | B | B | B | B | B | B | C | B | B |

EXAMPLE 2

A hair treating composition and two comparative formulations are shown in Table 9. The formulations were prepared by a method known per se in the art. Hair tresses of 15 g in weight were treated with each formulation at 30° C. for 10 minutes, and the results of treatment were evaluated in the same manner as in Example 1. The results are shown in Table 9.

TABLE 9

|  | Invention Product | Comparative Product | |
|---|---|---|---|
|  | 16 | 5 | 6 |
| N-Acetyl-L-cysteine | 1 | 1 | — |
| Polyoxyethylene lauryl ether (23 E.O.) | 3 | 3 | 3 |
| Stearyltrimethylammonium chloride (28%) | 1 | 1 | 1 |
| Adduct of pentaerythritol with 1 mol of isostearyl glycidyl ether (Synthetic Example 1) | 3 | — | 3 |
| Sodium hydroxide (48%) | 1 | 1 | 1 |
| Citric acid | ←Proper amount→ | | |
| Purified water | ←Balance→ | | |
| Total | 100 | 100 | 100 |
| pH | 7 | 7 | 7 |
| Organoleptic evaluation right after treatment: | A | A | B |
| Ease of combing in wet state | A | B | A |

TABLE 9-continued

|  | Invention Product | Comparative Product | |
|---|---|---|---|
|  | 16 | 5 | 6 |
| Softness in dry state | A | B | A |
| Gloss in dry state | A | B | A |
| Moisturizability in dry state | A | B | A |
| Surface appearance of the hair | A | B | B |

TABLE 9-continued

|  | Invention Product | Comparative Product | |
|---|---|---|---|
|  | 16 | 5 | 6 |
| Organoleptic evaluation after shampooing 10 times: | | | |
| Ease of combing in wet state | B | D | C |
| Softness in dry state | B | D | C |
| Smoothness in dry state | B | D | C |
| Gloss in dry state | B | D | C |
| Moisturizability in dry state | B | D | C |
| Surface appearance of the hair | B | D | C |

EXAMPLE 3

Two-pack curing compositions of the formulations shown in Table 10 were prepared in accordance with a method known per se in the art, and hair tresses each 15 g in weight were treated with the respective first- and second-package formulations at 30° C. for 10 minutes. The results of the treatment were evaluated in the same manner as in Example 1. The results are shown in Table 10.

TABLE 10

| Ingredient % | Invention Product 17 | Comparative Product 7 | Comparative Product 8 |
|---|---|---|---|
| First Package: | | | |
| N-Acetyl-L-cysteine | 1 | 1 | — |
| Polyoxyethylene lauryl ether (23 E.O.) | 3 | 3 | 3 |
| Stearyltrimethylammonium chloride (28%) | 1 | 1 | 1 |
| Isostearyltrismethylol | — | — | — |
| Sodium hydroxide (48%) | 1 | 1 | 1 |
| Citric acid | ←Proper amount→ | | |
| Purified water | ←Balance→ | | |
| Total | 100 | 100 | 100 |
| pH | 7 | 7 | 7 |
| Second-package: | | | |
| Polyoxyethylene lauryl ether sodium sulfate (23 E.O. (25%) | 3 | 3 | 3 |
| Isostearyltrismethylol | 3 | — | 3 |
| Sodium hydroxide (48%) | 1 | 1 | 1 |
| Citric acid | ←Proper Amount→ | | |
| Purified water | ←Balance→ | | |
| Total | 100 | 100 | 100 |
| pH | 7 | 7 | 7 |
| Organoleptic evaluation right after treatment: | | | |
| Ease of combing in wet state | A | c | B |
| Softness in dry state | A | c | B |
| Smoothness in dry state | A | c | B |
| Gloss in dry state | A | c | B |
| Moisturizability in dry state | A | c | B |
| Surface appearance of the hair | A | c | B |
| Organoleptic evaluation after shampooing 10 times: | | | |
| Ease of combing in wet state | B | D | c |
| Softness in dry state | B | D | c |
| Smoothness in dry state | B | D | c |
| Gloss in dry state | B | D | c |
| Moisturizability in dry state | B | D | c |
| Surface appearance of the hair | B | D | c |

EXAMPLE 4

First- and second-package formulations were prepared as shown below, as well as intermediate treatment formulations as shown in Table 11. The compositions were prepared by a method known per se in the art.

Tresses of 15 g in weight were treated with the first-package formulation for 10 minutes, followed by a treatment with the intermediate formulation for 5 minutes and then a treatment with the second-package formulation for 10 minutes. The permanent wave compositions were evaluated in the same manner as described in Example 1. The results are shown in Table 11.

(First-package):

| Ammonium thioglycolate solution (50%) | 14 (%) |
|---|---|
| Monoethanolamine | Proper amount (adjusted to pH 9) |
| Purified water | Balance |

(Second-package):

| Sodium bromate | 8 (%) |
|---|---|
| Purified water | Balance |

TABLE 11

| Ingredient (%) | Invention Product 18 | Comparative Product 9 |
|---|---|---|
| Polyoxyethylene lauryl ether (23 E.O.) | 3.0 | 3.0 |
| Stearyltrimethylammonium chloride (28%) | 0.3 | 0.3 |
| Methylisostearyltrismethyloamide | 3.0 | — |
| Sodium hydroxide (48%) | 1.0 | 1.0 |
| Citric acid | ←Proper amount→ | |
| Purified water | ←Balance→ | |
| Total | 100 | 100 |
| pH | 5 | 5 |
| Organoleptic evaluation right after treatment | | |
| Ease of combing in wet state | A | c |
| Softness in dry state | A | c |
| Smoothness in dry state | A | c |
| Gloss in dry state | A | c |
| Moisturizability in dry state | A | c |
| Surface appearance of the hair | A | c |
| Organoleptic evaluation after shampooing 10 times: | | |
| Ease of combing in wet state | B | D |
| Softness in dry state | B | D |
| Smoothness in dry state | B | D |
| Gloss in dry state | B | D |
| Moisturizability in dry state | B | D |
| Surface appearance of the hair | B | D |

EXAMPLE 5

First- and second-package formulations were prepared as shown below, as well as after treatment formulations as shown in Table 12. The compositions were prepared by a method known per se in the art.

Tresses of 15 g in weight were treated with the first-package formulation for 10 minutes, followed by a treatment with the second-package formulation for 10 minutes and then with an after treatment formulation for 5 minutes. The permanent wave compositions were evaluated in the same manner as described in Example 1. The results are shown in Table 12.

| (First-package): | |
|---|---|
| L-Cysteine | 6 (%) |
| Ammonium thioglycolate solution (50%) | 1.8 |
| Monoethanolamine | Proper amount (adjusted to pH 9) |
| Purified water | Balance |
| (Second-package): | |
| Sodium bromate | 8 (%) |
| Purified water | Balance |

TABLE 12

| Ingredient (%) | Invention Product 19 | Comparative Product 10 |
|---|---|---|
| Polyoxyethylene lauryl ether (23 E.O.) | 3.0 | 3.0 |
| Stearyltrimethylammonium chloride (28%) | 0.3 | 0.3 |

TABLE 12-continued

| Ingredient (%) | Invention Product 19 | Comparative Product 10 |
|---|---|---|
| Adduct of pentaerythritol with isostearyl glycidyl ether (Synthetic Example 2) | 3.0 | — |
| Sodium hydroxide (48%) | 1.0 | 1.0 |
| Citric acid | ←Proper amount→ | |
| Purified water | ←Balance→ | |
| Total | 100 | 100 |
| pH | 5 | 5 |
| Organoleptic evaluation right after treatment | | |
| Ease of combing in wet state | A | c |
| Softness in dry state | A | c |
| Smoothness in dry state | A | c |
| Gloss in dry state | A | c |
| Moisturizability in dry state | A | c |
| Surface appearance of the hair | A | c |
| Organoleptic evaluation after shampooing 10 times: | | |
| Ease of combing in wet state | B | D |
| Softness in dry state | B | D |
| Smoothness in dry state | B | D |
| Gloss in dry state | B | D |
| Moisturizability in dry state | B | D |
| Surface appearance of the hair | B | D |

What is claimed as new and desired to be secured by Letters Patent of the United States is:

1. A hair treatment composition consisting essentially of the following components:

(A) at least one keratin-reducing substance;

(B) at least one nonionic amphiphatic compound which contains at least one long-chain branched alkyl or alkenyl group per molecule, and which has an HLB of 2–12, said compound itself or a mixture of said compound and water maintaining a liquid crystal structure at a temperature ranging from 0°–5° C. which is at least one compound selected from the group consisting of compounds designated as (B-1) through (B-4):

(B-1):

glycerylated polyols of formula (1):

$$A_a(G) \qquad (1)$$

wherein G is the residue in which a hydroxyl group(s) has been eliminated from a polyol selected from the group consisting pentaerythritol, sorbitol, maltitol, glucose, and fructose;

A denotes $$-CH_2CHCH_2OR^1 \text{ and/or } HOCH_2CHCH_2OR^1$$
$$\quad\;\; | \qquad\qquad\qquad\qquad\qquad\quad |$$
$$\quad\;\; OH$$

in which $R^1$ is a branched alkyl or alkenyl group having 10–36 carbon atoms, and a is an integer of one up to the total number of the hydroxyl groups in the polyol;

(B-2):

methyl-branched fatty acid esters of formula (2):

$$CH_3(CH_2)_{b1}-CH-(CH_2)_{b2}-\overset{O}{\underset{\|}{C}}-O-CH_2\overset{CH_2OH}{\underset{|}{C}}-CH_2OH \qquad (2)$$
$$\qquad\qquad\quad | \qquad\qquad\qquad\qquad\qquad |$$
$$\qquad\qquad\quad CH_3 \qquad\qquad\qquad\qquad CH_2OH$$

wherein $b_1$ and $b_2$ are individually zero or an integer of 1–33, and the sum of $b_1$ and $b_2$ is 6–33;

(B-3):

branched fatty acid glyceroglycolipids of formula (3):

wherein $R^2$ is $$-(CH_2)_{c1}-CH-(CH_2)_{c2}-CH_3 \text{ or}$$
$$\qquad\qquad |$$
$$\qquad\qquad CH_3$$

$$-CH_2-CH-(CH_2)_{c3}-CH_3$$
$$\qquad\quad |$$
$$\qquad\quad CH_2(CH_2)_{c4}-CH_3$$

in which $c_1$ and $c_2$ are individually zero or an integer of 1–33, the sum of $c_1$ and $c_2$ is 6–33, $c_3$ and $c_4$ are individually zero or an integer of 1–31, and the sum of $c_3$ and $c_4$ is 4–31; and (B-4):

trismethylolamides of formula ( 5 ):

$$R^3-CONHC(CH_2OH)_3 \qquad (5)$$

wherein $R^3$ is a linear or branched alkyl group having 6–22 carbon atoms;

a compound of the formula:

wherein R is isostearyl;

(C) water; and (D) at least one additive selected from the group consisting of surfactants, oily substances, moisturizers, hair protecting agents, feel improvers, coloring matter, perfume bases, thickeners, solubilizing agents, ultraviolet absorbants, anti-phlogistics and hair growth ingredients.

2. The composition according to claim 1, wherein the amount of component (A) is 0.1–20.0 wt.% based on the whole hair treatment composition.

3. The composition according to claim 1, wherein the amount of component (B) is 0.05–10 wt. % based on the whole hair treatment composition.

4. The composition according to claim 1, wherein components (A) and (B) are present in amounts of 0.1–20.0 wt. % and 0.05–10 wt. % respectively, based on the whole hair treatment composition, and water is present at a weight ratio of from $99/1$ to $1/99$ to the component (B).

5. The composition according to claim 1, wherein the components (A) and (B) are separately incorporated in different formulations, or mixed with each other in the same formulation.

6. The composition according to claim 1, wherein the composition is in the form of a permanent wave composition, straight permanent wave composition, sustainable hair-setting composition, sustainable hair-curling composition or curled hair-straightening composition.

7. The composition according to claim 1, which has a pH within the range of 3.0 to 9.5.

8. The composition according to claim 1, wherein the component (A) is at least one substance selected from the group consisting of thioglycolic acid and salts thereof, glyceryl monothioglycolate, cysteine and salts thereof, thioglyceryl alkyl ethers, mercaptoalkylamides and salts thereof; thiolactic acid and salts thereof, sulfurous acid and salts thereof; and bisulfites.

9. The composition according to claim 1, wherein said component (A) is thioglycolic acid, and salts thereof and said component (B) is a compound of the formula:

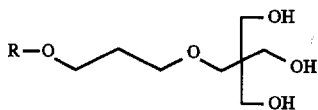

wherein R is isostearyl.

10. A method for treating the hair which comprises:

treating said hair with a formulation which consists essentially of a mixture of the following components:

(A) at least one keratin-reducing substance;

(B) at least one nonionic amphiphatic compound which contains at least one long-chain branched alkyl or alkenyl group per molecule, and which has an HLB of 2–12, said compound itself or a mixture of said compound and water maintaining a liquid crystal structure at a temperature ranging from 0°–50° C. which is at least one compound selected from the group consisting of compounds designated as (B-1) through (B-4):

(B-1):

glycerylated polyols of formula (1):

$$A_1(G) \tag{1}$$

wherein G is the residue in which a hydroxyl group(s) has been eliminated from a polyol selected from the group consisting of pentaerythritol, sorbitol, maltitol, glucose and fructose;

A denotes

in which $R^1$ is a branched alkyl or alkenyl group having 10–36 carbon atoms, and a is an integer of one up to the total number of the hydroxyl groups in the polyol;

(B-2):

methyl-branched fatty acid esters of formula (2):

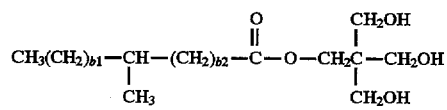

wherein $b_1$ and $b_2$ are individually zero or an integer of 1–33, and the sum of $b_1$ and $b_2$ is 6–33;

(B-3):

branched fatty acid glyceroglycolipids of formula (3):

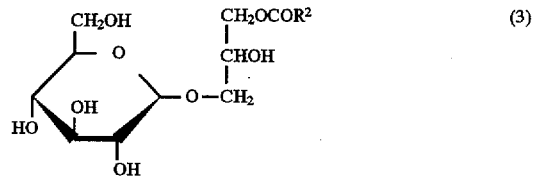

wherein $R^2$ is

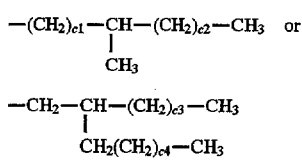

in which $c_1$ and $c_2$ are individually zero or an integer of 1–33, the sum of $c_1$ and $c_2$ is 6–33, $c_3$ and $c_4$ are individually zero or an integer of 1–31, and the sum of $c_3$ and $c_4$ is 4–31; and (B-4):

a compound of the formula:

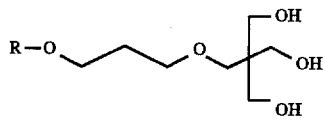

wherein R is isostearyl;

trismethylolamides of formula (5):

$$R^3\text{—CONHC}(CH_2OH)_3 \tag{5}$$

wherein $R^3$ is a linear or branched alkyl group having 6–22 carbon atoms;

(C) water; and (D) at least one additive selected from the group consisting of surfactants, oily substances, moisturizers, hair protecting agents, feel improvers, coloring matter, perfume bases, thickeners, solubilizing agents, ultraviolet absorbents, anti-phlogistics and hair growth ingredients.

11. A method for treating the hair which comprises:

successively treating the hair with a first formulation consisting essentially of component (A) and water and a second formulation consisting essentially of component (B) and water in this order; wherein (A) is at least one keratin-reducing substance;

(B) at least one nonionic amphiphatic compound which contains at least one long-chain branched alkyl or alkenyl group per molecule, and which has an HLB of 2–12, said compound itself or a mixture of said compound and water maintaining a liquid crystal structure at a temperature ranging from 0°–50° C. which is at least one compound selected from the group consisting of compounds designated as (B-1) through (B-4):

(B-1)

glycerylated polyols of formula (1):

$$A_a(G) \tag{1}$$

wherein G is the residue in which a hydroxyl group(s) has been eliminated from a polyol selected from the group consisting of pentaerythritol, sorbitol, maltitol, glucose and fructose;

A denotes

in which $R^1$ is a branched alkyl or alkenyl group having 10–36 carbon atoms, and a is an integer of one up to the total number of the hydroxyl groups in the polyol;

(B-2):

methyl-branched fatty acid esters of formula (2):

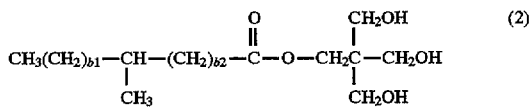

wherein $b_1$ and $b_2$ are individually zero or an integer of 1–33, and the sum of $b_1$ and $b_2$ is 6–33;

(B-3):

branched fatty acid glyceroglycolipids of formula (3):

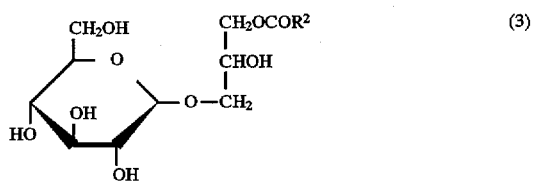

wherein $R^2$ is

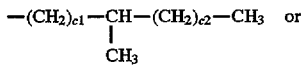 or

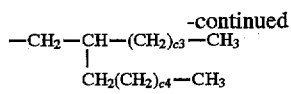

in which $c_1$ and $c_2$ are individually zero or an integer of 1–33, the sum of $c_1$ and $c_2$ is 6–33, $c_3$ and $c_4$ are individually zero or an integer of 1–31, and the sum of $c_3$ and $c_4$ is 4–31; and (B-4):

trismethylolamides of formula (5):

$$R^3-CONHC(CH_2OH)_3 \qquad (5)$$

wherein $R^3$ is a linear or branched alkyl group having 6–22 carbon atoms;

a compound of the formula:

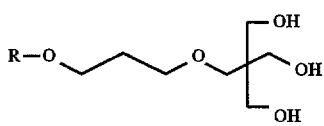

wherein R is isostearyl;

(C) water; and (D) at least one additive selected from the group consisting of surfactants, oily substances, moisturizers, hair protecting agents, feel improvers, coloring water, perfume bases, thickeners, solubilizing agents, ultraviolet absorbants, anti-phlogistics and hair growth ingredients.

* * * * *

UNITED STATES PATENT AND TRADEMARK OFFICE
CERTIFICATE OF CORRECTION

PATENT NO. : 5,665,338
DATED : September 9, 1997
INVENTOR(S) : Tadashi TANIMURA, et al.

It is certified that error appears in the above-identified patent and that said Letters Patent is hereby corrected as shown below:

Column 21, line 43, "$A_1(G)$" should read --$A_a(G)$

Signed and Sealed this

Thirteenth Day of January, 1998

BRUCE LEHMAN

*Attest:*

*Attesting Officer*         *Commissioner of Patents and Trademarks*